United States Patent
Li

(10) Patent No.: US 8,096,974 B2
(45) Date of Patent: Jan. 17, 2012

(54) SELF-DESTROYING DISPOSABLE SYRINGE AND SELF-DESTROYING METHOD THEREOF

(76) Inventor: Jianquan Li, Chongqing (CN)

( * ) Notice: Subject to any disclaimer, the term of this patent is extended or adjusted under 35 U.S.C. 154(b) by 110 days.

(21) Appl. No.: 12/294,454

(22) PCT Filed: Mar. 28, 2007

(86) PCT No.: PCT/CN2007/001009
§ 371 (c)(1),
(2), (4) Date: Jul. 1, 2010

(87) PCT Pub. No.: WO2007/115481
PCT Pub. Date: Oct. 18, 2007

(65) Prior Publication Data
US 2010/0280453 A1 Nov. 4, 2010

(30) Foreign Application Priority Data
Mar. 28, 2006 (CN) .................... 2006 2 0110211 U

(51) Int. Cl.
*A61M 5/00* (2006.01)
*A61M 5/315* (2006.01)
(52) U.S. Cl. ................. 604/110; 604/218; 604/240
(58) Field of Classification Search .................. 604/110, 604/111, 181, 187, 218, 228, 240, 243, 221, 604/222
See application file for complete search history.

(56) References Cited

U.S. PATENT DOCUMENTS
4,950,253 A 8/1990 Jacobs
5,246,423 A * 9/1993 Farkas .......................... 604/110
5,968,021 A 10/1999 Ejlersen OTHER PUBLICATIONS
International Search Report dated Jul. 19, 2007 (PCT/CN07/01009) ISA/CN.

* cited by examiner

*Primary Examiner* — Nicholas D Lucchesi
*Assistant Examiner* — Leah Stohr
(74) *Attorney, Agent, or Firm* — Banner & Witcoff, Ltd.

(57) ABSTRACT

A self-destroying disposable syringe includes a barrel which includes a hub disposed on the front end of the barrel, a flange is disposed on the inner wall of the hub; a needle base which connects to the hub of the barrel, and includes a connecting portion, a containing portion disposed on the outer side of the connecting portion, and a self-destroying ring disposed on the back end of the needle base and connected to the connecting portion through one or more ribs; when the needle base has connected to the barrel, the connecting portion and the self-destroying ring are located in the inside of the hub of the barrel, and the self-destroying ring matches the flange each other; a plunger which is movably inserted into the barrel and includes a bar body, a pushing stem connected to the back end of the bar body, a pushing dish connected to the front end of the bar body, a cone with one end fixed to the pushing disc, and a puncturing portion fixed to the other end of the cone; and a piston which is connected to the cone of the plunger, a cavity is provided within the piston; a sealed front wall is provided on the front end of the piston, an opening communicated with the cavity is provided on the back end of the piston.

25 Claims, 4 Drawing Sheets

SELF-DESTROYING DISPOSABLE SYRINGE AND SELF-DESTROYING METHOD THEREOF

BACKGROUND OF THE INVENTION

The present invention relates to a disposable syringe in the field of medical apparatus, and in particular to a self-destroying disposable syringe and a self-destroying method thereof.

It is a trend that the disposable syringe is used for substituting the reusable syringe, and there have been various types of disposable syringes. A self-destroying syringe disclosed in Chinese patent application no. 200320110786.X and a self-destroying syringe disclosed in Chinese patent application no. 03266160.6 develop in the aspect of avoiding the reuse of syringe. However, there are still some problems, for example, in the former, the self-destroying characteristic is poor due to only a plug fitting with a plug cavity, while in the latter, the configuration is complex for manufacturing. In another Chinese patent application no. 200420105856.7, another self-destroying disposable syringe as shown in FIG. 1 is disclosed, the syringe comprising a needle base 1, a barrel 2, a pushing stem 3, and a piston 4, wherein the end of the needle base 1 is provided with a dual self-destroying ring, the front end of the pushing stem 3 is provided with a hub for fitting with the piston 4, while the rear end is provided with a pawl for interlocking with a self-locking ring of the barrel 2. Though the syringe with the above structure can achieve the function of self-destroying, there are still some problems: 1. the needle base structure is complex and thus increases the resistance to self-destroy, which affects the self-destroy result; 2. the tip end and the spherical protrusion of the pushing stem 3 are hard for manufacturing; 3. the front end of the pushing stem 3 is provided with a pushing disc for fitting with the barrel 2 and sealed by the piston 4, and during the pushing process, negative pressure and resistance may be generated, which goes against the injection; 4. the piston 4 is of abnormal shape and consequently hard for manufacturing.

SUMMARY OF THE INVENTION

It is an objective of the present invention to provide a self-destroying disposable syringe, which is of simple structure and good self-destroying result, and is easy for assembly and use, so as to overcome the defects lying in the prior art.

It is another objective of the present invention to provide a self-destroying method of disposable syringe, to simplify the structure of disposable syringe and improve the self-destroying result.

To achieve the above objectives, the present invention provides a self-destroying disposable syringe, comprising: a barrel which includes a hub disposed on the front end of the barrel, a flange is disposed on the inner wall of the hub; a needle base which connects to the hub of the barrel, and includes a connecting portion, a containing portion disposed on the outer side of the connecting portion, and a self-destroying ring disposed on the back end of the needle base and connected to the connecting portion through one or more ribs; when the needle base has connected to the barrel, the connecting portion and the self-destroying ring are located in the inside of the hub of the barrel, and the self-destroying ring matches the flange each other; a plunger which is movably inserted into the barrel and includes a bar body, a pushing stem connected to the back end of the bar body, a pushing dish connected to the front end of the bar body, a cone with one end fixed to the pushing disc, and a puncturing portion fixed to the other end of the cone; and a piston which is connected to the cone of the plunger, a cavity for containing the puncturing portion is provided within the piston; a sealed front wall is provided on the front end of the piston, an opening communicated with the cavity is provided on the back end of the piston.

Preferably, the plunger is provided with a vent groove extending through the puncturing portion, the cone and the pushing disc.

Preferably, the puncturing portion of the plunger comprises a puncturing tip and a puncturing stem connecting the puncturing tip with the cone, wherein the diameter of the puncturing tip is larger than the diameter of the puncturing stem at the joint of the puncturing tip and the puncturing stem.

Preferably, the cone of the plunger comprises a first cone portion connected to the puncturing portion and a second cone portion connected to the pushing disc, an annular groove is provided between the first cone portion and the second cone portion.

Preferably, the rear end of the piston is provided with a protrusion for fitting with the annular groove of the cone.

Preferably, the cavity of the piston comprises a first cavity adjacent to the front end of the piston and a second cavity adjacent to the rear end of the piston, the diameter of the first cavity being larger than the diameter of the second cavity.

Preferably, the outer wall of the piston is provided with one or more annular protrusions for fitting with the inner wall of the barrel.

Preferably, the front end of the piston is provided with a recess for fitting with the self-destroying ring.

Preferably, the piston is made of elastic materials.

Preferably, the diameter of the pushing disc is larger than the diameter of the bar body.

Preferably, the inner wall of the barrel is provided with an inward protrusion near the rear end of the barrel, the inward protrusion being designed with structure and dimension to fit with the pushing disc.

Preferably, the self-destroying ring of the needle base is provided with an axial opening.

Preferably, the outer wall of the self-destroying ring is provided with an annular groove such that when the needle base is connected to the hub of the barrel, the flange on the inner wall of the hub is located in the groove of the self-destroying ring.

Preferably, the flange of the hub is protruded inwards and backwards from the inner wall of the hub.

Preferably, the outer wall of the connecting portion of the needle base is provided with a sealing ring for fitting with the inner wall of the hub.

The present invention further provides a self-destroying method of disposable syringe. The method comprises the following steps: a) providing a barrel having a hub on the front end of the barrel and a flange on the inner wall of the hub; b) providing a needle base comprising a connecting portion, a containing portion disposed on the outer side of the connecting portion, and a self-destroying ring disposed on the back end of the needle base and connected to the connecting portion through one or more ribs; c) providing a plunger a bar body, a pushing stem connected to the back end of the bar body, a pushing dish connected to the front end of the bar body, a cone with one end fixed to the pushing disc, and a puncturing portion fixed to the other end of the cone; d) providing a piston having a cavity inside for containing the puncturing portion, a sealed front wall on the front end of the piston, an opening communicated with the cavity on the back end of the piston; e) connecting the needle base to the barrel such that the connecting portion and the self-destroying ring are located inside the hub of the barrel, and the self-destroying ring matches the flange each other; f) connecting the piston with the cone of the plunger; g) inserting the plunger into the barrel such that the piston is located inside the barrel and moves together with the plunger with respect to the barrel; h) further moving the plunger to self-destroy the syringe after the injection process is finished.

Preferably, the step h) further comprises: pushing the plunger to allow the puncturing portion to puncture through the front wall of the piston; further pushing the plunger to allow the puncturing portion to puncture through the self-destroying ring; and separating the connecting portion of the needle base from the self-destroying ring by pushing the plunger.

Preferably, the puncturing portion comprises a puncturing tip and a puncturing bar connecting the puncturing tip with the cone, wherein at the joint of the puncturing tip and the puncturing bar, the diameter of the puncturing tip is larger than the diameter of the puncturing bar.

Preferably, the method further comprises: pushing the plunger to allow the puncturing tip to puncture through the self-destroying ring.

According to one aspect of the present invention, the syringe is provided with multiple self-destroying measures, so as to ensure the safe use of the syringe. Particularly, firstly, after the injection is finished, the puncturing portion of the plunger is capable to force the self-destroying ring to depart from the needle base and lock within the hub, so that the syringe is self-destroyed; secondly, after the self-destroying of the syringe, the self-locking ring in the barrel is connected to the plunger and the piston in one, and locked by the flange on the inner wall of the hub, such that the plunger can not move with respect to the barrel; thirdly, after the self-destroying of the syringe, the vent groove on the plunger communicates the two spaces of the barrel in front of the piston and in back of the piston, thus the barrel is no longer able to absorb liquid medicine; fourthly, even if the plunger is pulled by a strong force, the piston on the front end of the plunger will disengage from the plunger and remain within the barrel, which once again ensures the barrel not to be reused.

According to another aspect of the present invention, the resistance is small during the self-destroying of the syringe, which is convenient for operating. For an opening is provided on the self-destroying ring, the resistance is significantly reduced during the self-destroying of the syringe. Furthermore, the vent groove on the front end of the plunger enables the front space and the back space of the barrel communicates with each other, and no negative pressure occurs, which also reduce the resistance during the self-destroying.

According to another aspect of the present invention, the syringe of the present invention is of simple structure and convenient for assembly and use; and the parts of the syringe are easy for manufacturing. Moreover, the cost of the syringe of the present invention is only a little higher than that of a normal disposable syringe, but the syringe of the present invention is of high safety and advantageous for promotion.

According to another aspect of the present invention, it is unnecessary for the medical staff to destroy the syringe manually, which prevents the medical staff from being injured accidentally and subsequently infected.

According to still another aspect of the present invention, after the syringe of the present invention is self-destroyed, the metallic needle can be separated from the other parts of the syringe, and the metallic materials and the plastic materials may be recycled, which is good for environment protection.

DETAILED DESCRIPTION OF THE INVENTION

The present invention will further described in the following embodiments accompanying with the drawings.

Figure 1:
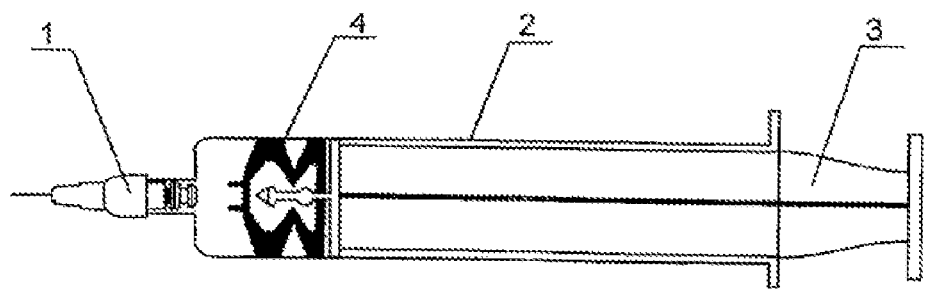
FIG. 1 is a schematic structural view of a known disposable syringe.
Figure 2:
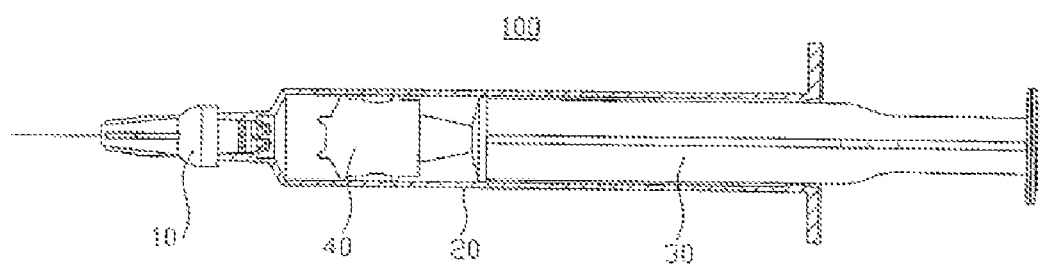
FIG. 2 is a schematic structural view of a disposable syringe according to a preferred embodiment of the present invention.

Referring to FIG. 2, the syringe 100 comprises a barrel 20, a needle base 10 connected to the barrel 20, a plunger 30 in the barrel 20 and being movable with respect to the barrel 20, and a piston 40 connected to the front end of the plunger 30. Preferably, the barrel 20 and the plunger 30 are made of plastic, while the piston 40 is made of elastic materials such as rubber.

Figure 3A:
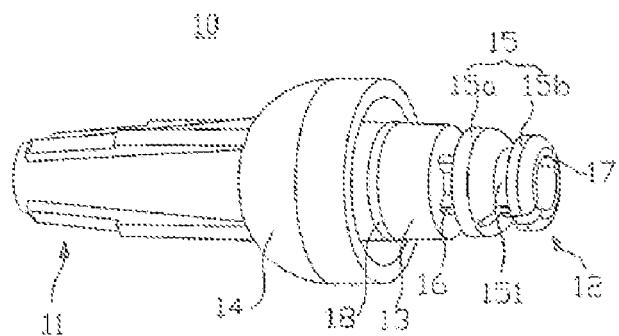
FIG. 3A is a perspective view of the needle base shown in FIG. 2.
Figure 3B:
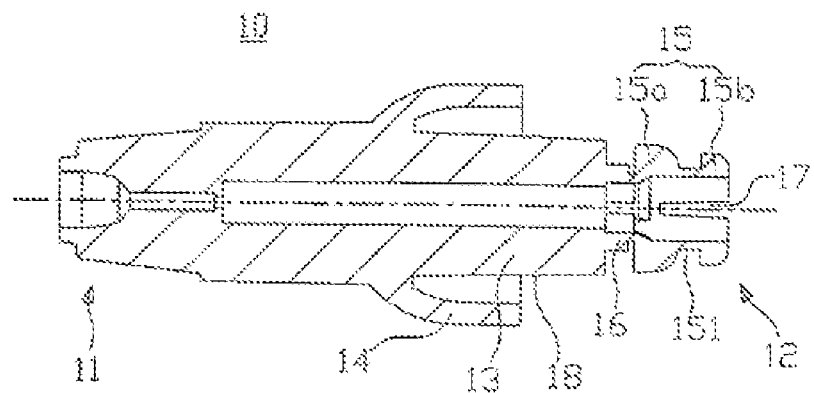
FIG. 3B is a cross-sectional view of the needle base shown in FIG. 3A.

Referring to FIG. 3A and FIG. 3B, the needle base 10 comprises a connecting portion 13, a containing portion 14 provided outside the connecting portion 13. The rear end 12 of the needle base 10 is provided with a self-destroying ring 15, and the self-destroying ring 15 is connected to the connecting portion through one or more ribs 16. The front end 11 of the needle base 10 is used for connecting a needle for injection (not shown). Preferably, the self-destroying ring 15 is provided with an axial opening 17. According to an embodiment of the present invention, the outer wall of the self-destroying ring 15 is provided with an annular groove 151 which divides the self-destroying ring 15 into a first portion 15a and a second portion 15b. The axial opening penetrates through the second portion 15b and the annular groove 151, and penetrates partially into the first portion 15a.

Figure 4A:
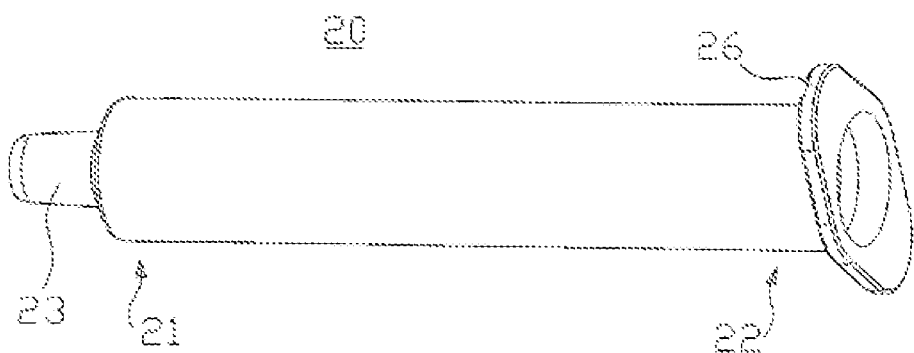
FIG. 4A is a perspective view of the barrel shown in FIG. 2.
Figure 4B:
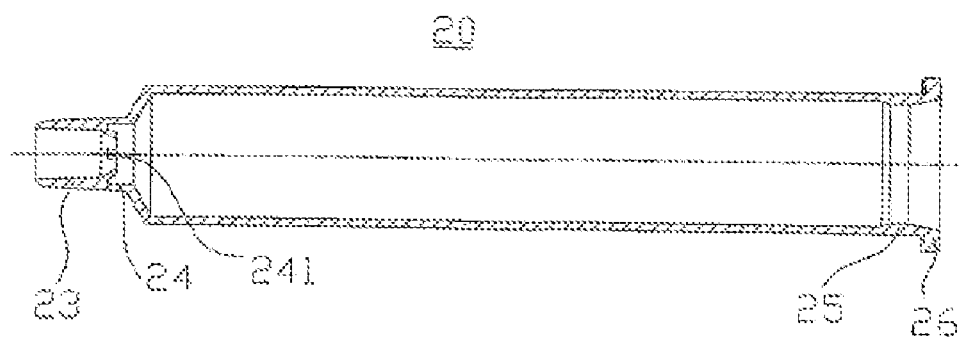
FIG. 4B is a cross-sectional view of the barrel shown in FIG. 4A.

Referring to FIGS. 4A and 4B, the barrel 20 is hollow, the front end 21 of the barrel 20 is provided with a hub 23 for connecting with the needle base 10, while the rear end 22 of the barrel 20 is provided with an ear 26 for facilitating injection. A flange 24 protrudes from the inner wall of the hub 23. Preferably, the flange 24 protrudes obliquely towards the rear end of the barrel 20. When the needle base 10 has connected to the hub 23 of the barrel 20, the connecting portion 13 and the self-destroying ring 15 are located in the inside of the hub 23 of the barrel 20, and the self-destroying ring 15 matches with the flange 24. Preferably, the outer wall of the connecting portion 13 of the needle base 23 is provided with a sealing ring 18 (as shown in FIG. 3A) for fitting with the inner wall of the hub 23, and thus the sealing performance between the needle base 10 and the barrel 20 is improved in normal use.

Figure 5A:
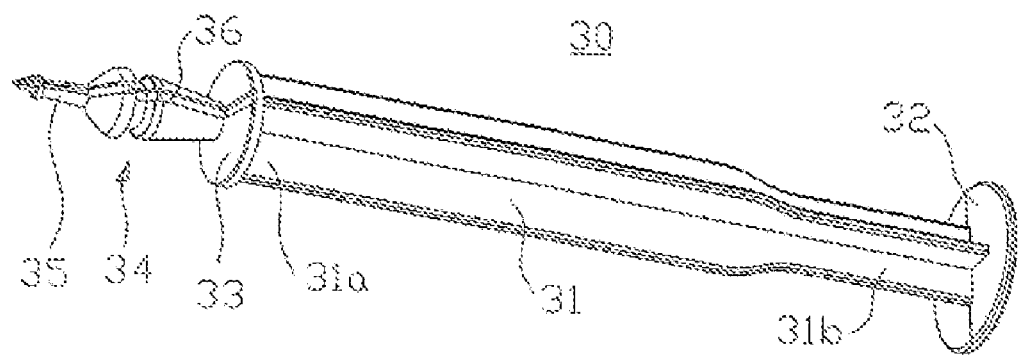
FIG. 5A is a perspective view of the plunger shown in FIG. 2.
Figure 5B:
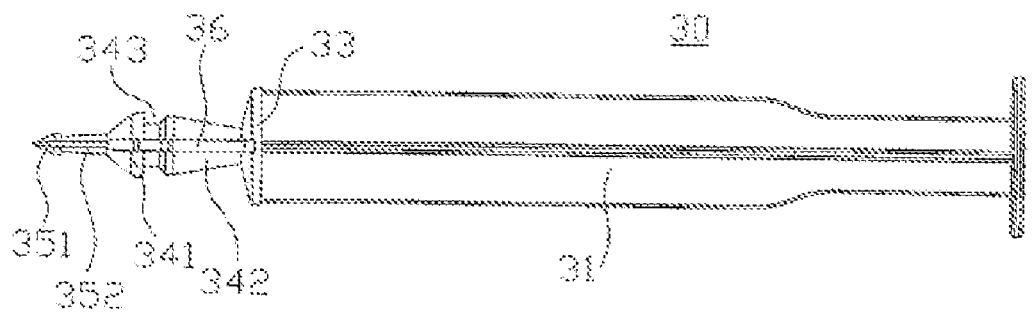
FIG. 5B is a plan view of the plunger shown in FIG. 5A.

Referring to FIGS. 5A and 5B, the plunger 30 a bar body 31, a pushing stem 32 connected to the back end 31b of the bar body 31, a pushing dish 33 connected to the front end 31a of the bar body 31, a cone 34 with one end fixed to the pushing disc 33, and a puncturing portion 35 fixed to the other end of the cone 34. Preferably, the diameter of the pushing disc 33 is larger than that of the bar body 31. As shown in FIG. 4B, the inner wall of the barrel 20 is provided with an inward protrusion 25 near the rear end 22 of the barrel 20, and the inward protrusion 25 is designed with structure and dimension to fit with the pushing disc 33. Preferably, the plunger 30 is provided with a vent groove 36 extending through the puncturing portion 35, the cone 34 and the pushing disc 33. The cone 34 matches with the piston 40. Particularly, the piston 40 is connected to the cone 34, such that the piston 40 can move together with the plunger 30 with respect to the barrel 20 in normal use. According to an embodiment of the present invention, the cone 34 comprises a first cone portion 341 connected to the puncturing portion 35 and a second cone portion 342 connected to the pushing disc 33, an annular groove 343 being provided between the first cone portion 341 and the second cone portion 342. The puncturing portion 35 comprises a puncturing tip 351 and a puncturing stem 352 connecting the puncturing tip 351 with the cone 34. Preferably, the diameter of the puncturing tip 351 is larger than the diameter of the puncturing stem 352 at the joint of the puncturing tip 351 and the puncturing stem 352.

Figure 6:
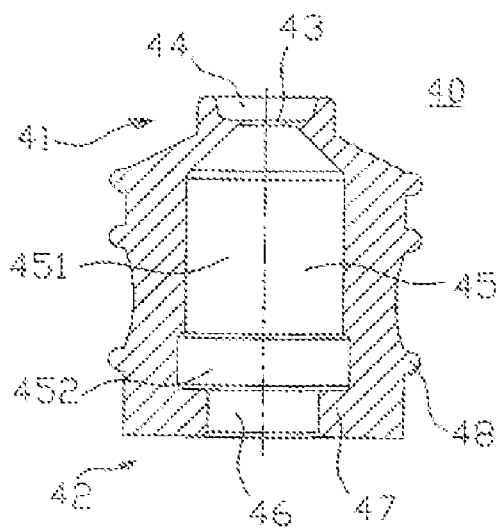
FIG. 6 is a cross-sectional view of the piston shown in FIG. 2.

As shown in FIG. 6, a cavity 45 is provided within the piston 40. The front end 41 of the piston 40 is provided with a closed front wall 43, while the rear end 42 of the piston 40 is provided with an opening 46 which communicates with the cavity 45. The outer wall of the piston is provided with one or more annular protrusions 48 for fitting with the inner wall of the barrel 20, so as to improve the sealing performance between the piston 40 and the barrel 20. Preferably, the front end 41 of the piston is provided with a recess 44 for fitting with the self-destroying ring 15, in order to minimize the remaining liquid medicine in the barrel 20. The recess 44 also reduces the thickness of the front wall 43. The rear end 42 of the piston is provided with a protrusion 47 for fitting with the annular groove 343 of the cone 34. Preferably, the cavity 45 of the piston comprises a first cavity 451 adjacent to the front end 41 of the piston and a second cavity 452 adjacent to the rear end 42 of the piston, and the diameter of the first cavity 451 is larger than the diameter of the second cavity 452.

Figure 7:
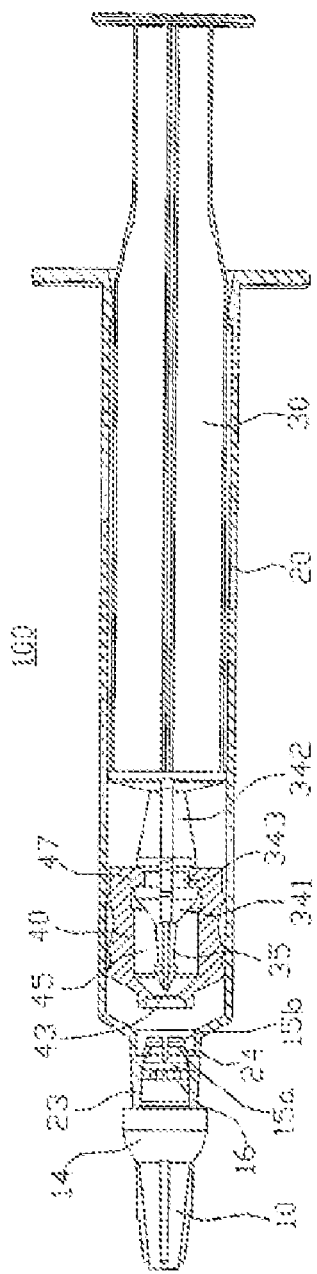
FIG. 7 is a cross-sectional view of the syringe in use according to the preferred embodiment of the present invention.

FIG. 7 shows a syringe 100 in normal use. The piston 40 is inside the barrel 20, the protrusion 47 matches with the annular groove 343, the piston together with the 40 can move within the barrel 20. The puncturing portion 35 of the plunger and the first cone portion 341 are located in the cavity 45, while the second cone portion 342 is located outside the cavity 45. The connecting portion 13 of the needle base and the self-destroying ring 15 are located within the hub 23; the containing portion 14 surrounds the hub 23 to improve the sealing between the needle base and the barrel. The flange 24 on the inner wall of the hub is located in the annular groove 151 so as to fit with the self-destroying ring to prevent the needle base 10 from departing from the barrel 20.

After the injection is finished, the plunger 30 is further pushed forward to realize the self-destroying of the syringe 100. Particularly, after the injection is finished, the second portion 15b of the self-destroying ring is in the recess 44 on the front end of the piston such that the front wall 43 of the piston 40 is attached to the self-destroying ring 15. For the piston 40 is made of elastic materials, the plunger 30 can be further pushed to deform the protrusion 47 of the rear end of the piston, such that the plunger 30 can be further moved with respect to the piston 40. The movement of the plunger 30 enables the second cone portion 342 to run through the opening 46 into the cavity 45, and the puncturing portion 35 punctures through the front wall 41 of the piston as well as the self-destroying ring 15. The resistance during the cone 34 moving in the cavity 45 is reduced since the diameter of the second cavity 452 is larger than that of the first cavity 453. Moreover, the opening 17 on the self-destroying ring 15 can reduce the resistance during the puncturing portion 35 puncturing through the self-destroying ring. The ribs 16 connecting the self-destroying ring 15 with the connecting portion 13 is designed into a structure which is unable to resist a pulling force and easy to break. When the plunger is further pushed forward, the puncturing portion 35 puncturing through the self-destroying ring 15 contacts and presses on the connecting portion 13, so as to break the ribs and thus the self-destroying ring 15 is departed from the needle base 10. Meanwhile, the needle base 10 is departed from the hub upon the push of the puncturing portion 35 and falls into for example a wastebin. In this way, the syringe 100 is self-destroyed.

Figure 8:
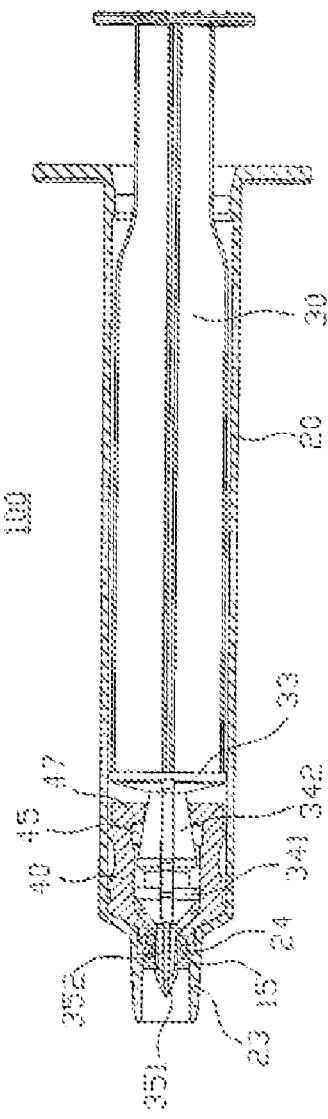
FIG. 8 is a cross-sectional view of the syringe after self-destroying, where the needle base is removed.

The self-destroyed syringe is shown in FIG. 8. The puncturing tip 351 punctures through the self-destroying ring 15 such that the self-destroying ring 15 sleeves on the puncturing stem 352. For the diameter of the puncturing tip 351 is larger than the diameter of the puncturing stem 352 at the joint of the puncturing tip 351 and the puncturing stem 352, the puncturing portion 35 is hard to be withdrawn from the self-destroying ring 15. Meanwhile, the flange 24 on the hub of the barrel is still in the groove 151 of the self-destroying ring. In this way, the self-destroying ring 15, the piston 40 and the plunger 30 are connected in one, and the flange 24 is locked within the barrel, therefore the self-destroyed syringe can not be used again. During the self-destroying of the syringe, the flange 24 arranged obliquely and backwards is better for locking the self-destroying ring 15, and thus the self-destroying ring 15 is prevented from being pushed out of the hub 23 by the puncturing portion 35.

Furthermore, for the vent groove 36 extends through the puncturing portion 35, the cone 34 and the pushing disc 33, the space in front of the piston 40 and the space in back of the piston 40 communicate with each other, and thus the syringe can not absorb liquid medicine after self-destroying. In this way, even if the self-destroying ring is destroyed while the plunger is drawn out by a strong force, the syringe can not be used again after self-destroying. Therefore, the save use of the syringe is ensured.

In addition, the protrusion 25 of the barrel fits with the pushing disc 33 of the plunger, so that the pushing disc 33 is hard to withdraw from the barrel 20. Thus, once the engagement between the protrusion 25 and the pushing disc 33 is destroyed by a strong force and consequently the plunger 30 is drawn out of the barrel 20, the piston 40 will remain in the barrel 20 due to the blocking of the protrusion 25, so that the syringe can not be used again.

It is seen from the above description that the syringe of the present invention is of a multiple self-destroying structure, which ensures the safe use of the disposable syringe while an embodiment of the invention and a method of the invention have been described, the invention is defined and limited only by the following claims and equivalents thereto.

What is claimed is:
1. A self-destroying disposable syringe, comprising:
a barrel having a hub on the front end of the barrel and a flange on the inner wall of the hub;
a needle base connected to the hub of the barrel, the needle base comprising a connecting portion, a containing portion disposed on the outer side of the connecting portion, and a self-destroying ring disposed on the back end of the needle base and connected to the connecting portion through one or more ribs, said one or more ribs being breakable; when the needle base is connected to the barrel, the connecting portion and the self-destroying ring are located in the inside of the hub of the barrel, and the self-destroying ring matches the flange of the barrel;

a plunger movably inserted into the barrel and comprising a bar body, a pushing stem connected to the back end of the bar body, a pushing disc connected to the front end of the bar body, a cone with one end fixed to the pushing disc, and a puncturing portion fixed to the other end of the cone, said puncturing portion being designed for puncturing through said self-destroying ring after injection for breaking said one or more ribs; and a piston connected to the cone of the plunger, a cavity for containing the puncturing portion being provided within the piston, a sealed front wall being provided on the front end of the piston, an opening communicated with the cavity being provided on the back end of the piston.

2. The self-destroying disposable syringe of claim 1, wherein the plunger is provided with a vent groove extending through the puncturing portion, the cone and the pushing disc.

3. The self-destroying disposable syringe of claim 1, wherein the puncturing portion of the plunger comprises a puncturing tip and a puncturing stem connecting the puncturing tip with the cone, wherein the diameter of the puncturing tip is larger than the diameter of the puncturing stem at the joint of the puncturing tip and the puncturing stem.

4. The self-destroying disposable syringe of claim 1, wherein the cone of the plunger comprises a first cone portion connected to the puncturing portion and a second cone portion connected to the pushing disc, an annular groove is provided between the first cone portion and the second cone portion.

5. The self-destroying disposable syringe of claim 4, wherein the rear end of the piston is provided with a protrusion for fitting with the annular groove of the cone.

6. The self-destroying disposable syringe of claim 1, wherein the cavity of the piston comprises a first cavity adjacent to the front end of the piston and a second cavity adjacent to the rear end of the piston, the diameter of the first cavity being larger than the diameter of the second cavity.

7. The self-destroying disposable syringe of claim 1, wherein the outer wall of the piston is provided with one or more annular protrusions for fitting with the inner wall of the barrel.

8. The self-destroying disposable syringe of claim 1, wherein the front end of the piston is provided with a recess for fitting with the self-destroying ring.

9. The self-destroying disposable syringe of claim 1, wherein the piston is made of elastic materials.

10. The self-destroying disposable syringe of claim 1, wherein the diameter of the pushing disc is larger than the diameter of the bar body.

11. The self-destroying disposable syringe of claim 10, wherein the inner wall of the barrel is provided with an inward protrusion near the rear end of the barrel, the inward protrusion being designed with structure and dimension to fit with the pushing disc.

12. The self-destroying disposable syringe of claim 1, wherein the self-destroying ring of the needle base is provided with an axial opening.

13. The self-destroying disposable syringe of claim 1, wherein the outer wall of the self-destroying ring is provided with an annular groove such that when the needle base is connected to the hub of the barrel, the flange on the inner wall of the hub is located in the groove of the self-destroying ring.

14. The self-destroying disposable syringe of claim 1, wherein the flange of the hub is protruded inwards and backwards from the inner wall of the hub.

15. The self-destroying disposable syringe of claim 1, wherein the outer wall of the connecting portion of the needle base is provided with a sealing ring for fitting with the inner wall of the hub.

16. A self-destroying method of disposable syringe, comprising the following steps:
a) providing a barrel having a hub on the front end of the barrel and a flange on the inner wall of the hub;
b) providing a needle base comprising a connecting portion, a containing portion disposed on the outer side of the connecting portion, and a self-destroying ring disposed on the back end of the needle base and connected to the connecting portion through one or more ribs, said one or more ribs being breakable;
c) providing a plunger a bar body, a pushing stem connected to the back end of the bar body, a pushing disc connected to the front end of the bar body, a cone with one end fixed to the pushing disc, and a puncturing portion fixed to the other end of the cone;
d) providing a piston having a cavity inside for containing the puncturing portion, a sealed front wall on the front end of the piston, an opening communicated with the cavity on the back end of the piston;
e) connecting the needle base to the barrel such that the connecting portion and the self-destroying ring are located inside the hub of the barrel, and the self-destroying ring matches the flange each other;
f) connecting the piston with the cone of the plunger;
g) inserting the plunger into the barrel such that the piston is located inside the barrel and moves together with the plunger with respect to the barrel;
h) further moving the plunger to self-destroy the syringe after the injection process is finished, said one or more ribs being destructed after the injection.

17. The method of claim 16, wherein the step h) further comprises: pushing the plunger to allow the puncturing portion to puncture through the front wall of the piston; further pushing the plunger to allow the puncturing portion to puncture through the self-destroying ring; and separating the connecting portion of the needle base from the self-destroying ring by pushing the plunger.

18. The method of claim 17, wherein the puncturing portion comprises a puncturing tip and a puncturing bar connecting the puncturing tip with the cone, wherein at the joint of the puncturing tip and the puncturing bar, the diameter of the puncturing tip is larger than the diameter of the puncturing bar.

19. The method of claim 18, wherein the method further comprises: pushing the plunger to allow the puncturing tip to puncture through the self-destroying ring.

20. A self-destroying disposable syringe, comprising:
a barrel having a hub on the front end of the barrel and a flange on the inner wall of the hub;
a needle base connected to the hub of the barrel, the needle base comprising a connecting portion, a containing portion disposed on the outer side of the connecting portion, and a self-destroying ring disposed on the back end of the needle base and connected to the connecting portion through one or more ribs, said one or more ribs being breakable; when the needle base is connected to the barrel, the connecting portion and the self-destroying ring are located in the inside of the hub of the barrel, and the self-destroying ring matches the flange of the barrel;
a plunger movably inserted into the barrel and comprising a bar body, a pushing stem connected to the back end of the bar body, a pushing disc connected to the front end of the bar body, a cone with one end said to the pushing disc, and a puncturing portion fixed to the other end of the cone, said puncturing portion being designed for puncturing through said self-destroying ring after injection for breaking said one or more ribs;

said cone of said plunger comprising a first cone portion connected to the puncturing portion and said second cone portion being connected to the pushing disc, an annular groove being provided between said first cone portion and said second cone portion; and a piston connected to the cone of the plunger, a cavity for containing the puncturing portion being provided within the piston, a sealed front wall being provided on the front end of the piston, an opening communicated with the cavity being provided on the back end of the piston.

21. The self-destroying disposable syringe of claim 20, wherein the rear end of the piston is provided with a protrusion for fitting with the annular groove of the cone.

22. A self-destroying disposable syringe, comprising:

a barrel having a hub on the front end of the barrel and a flange on the inner wall of the hub;

a needle base connected to the hub of the barrel, the needle base comprising a connecting portion, a containing portion disposed on the outer side of the connecting portion, and a self-destroying ring disposed on the back end of the needle base and connected to the connecting portion through one or more ribs, said one or more ribs being breakable; when the needle base is connected to the barrel, the connecting portion and the self-destroying ring are located in the inside of the hub of the barrel, and the self-destroying ring matches the flange of the barrel;

a plunger movably inserted into the barrel and comprising a bar body, a pushing stem connected to the back end of the bar body, a pushing disc connected to the front end of the bar body, a cone with one end fixed to the pushing disc, and a puncturing portion fixed to the other end of the cone, said puncturing portion being designed for puncturing through said self-destroying ring after injection for breaking said one or more ribs;

said pushing disc having a diameter larger than the diameter of the bar body, and the inner wall of said barrel being provided with an inward protrusion near the rear end of said barrel, said inward protrusion being designed with structure and dimensions to fit with said pushing disc;

a piston connected to the cone of the plunger, a cavity for containing the puncturing portion being provided within the piston, a sealed front wall being provided on the front end of the piston, an opening communicated with the cavity being provided on the back end of the piston.

23. A self-destroying method of disposable syringe, comprising the following steps:

a) providing a barrel having a hub on the front end of the barrel and a flange on the inner wall of the hub;

b) providing a needle base comprising a connecting portion, a containing portion disposed on the outer side of the connecting portion, and a self-destroying ring disposed on the back end of the needle base and connected to the connecting portion through one or more ribs;

c) providing a plunger a bar body, a pushing stem connected to the back end of the bar body, a pushing disc connected to the front end of the bar body, a cone with one end fixed to the pushing disc, and a puncturing portion fixed to the other end of the cone;

d) providing a piston having a cavity inside for containing the puncturing portion, a sealed front wall on the front end of the piston, an opening communicated with the cavity on the back end of the piston;

e) connecting the needle base to the barrel such that the connecting portion and the self-destroying ring are located inside the hub of the barrel, and the self-destroying ring matches the flange each other;

f) connecting the piston with the cone of the plunger;

g) inserting the plunger into the barrel such that the piston is located inside the barrel and moves together with the plunger with respect to the barrel;

h) further moving the plunger to self-destroy the syringe after the injection process is finished;

i) pushing said plunger for allowing said puncturing portion to puncture through the front wall of said piston and further pushing said plunger to allow the puncturing portion to puncture through the self-destroying ring; and separating the connecting portion of said needle base from the self-destroying ring by pushing said plunger.

24. The method of claim 23, wherein the puncturing portion comprises a puncturing tip and a puncturing bar connecting the puncturing tip with the cone, wherein at the joint of the puncturing tip and the puncturing bar, the diameter of the puncturing tip is larger than the diameter of the puncturing bar.

25. The method of claim 24, wherein the method further comprises: pushing the plunger to allow the puncturing tip to puncture through the self-destroying ring.

* * * * *